(12) United States Patent
Ignatchenko et al.

(10) Patent No.: US 6,521,765 B1
(45) Date of Patent: Feb. 18, 2003

(54) PROCESS FOR THE PREPARATION OF 3-METHYLTETRAHYDROFURAN

(75) Inventors: Alexey Victorovitch Ignatchenko, Longview, TX (US); William Anthony Beavers, Longview, TX (US); Zhufang Liu, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/125,664

(22) Filed: Apr. 18, 2002

(51) Int. Cl.$^7$ .................. C07D 307/08; C07D 307/06
(52) U.S. Cl. .................. 549/509; 549/429; 549/497; 549/508
(58) Field of Search ................ 549/509, 429, 549/497, 508

(56) References Cited

U.S. PATENT DOCUMENTS

| | | |
|---|---|---|
| 3,859,369 A | 1/1975 | Copelin |
| 3,932,468 A | 1/1976 | Kurkov |
| 4,590,312 A | 5/1986 | Ernst |
| 4,783,559 A | 11/1988 | Matsushita et al. |
| 4,810,825 A | 3/1989 | Matsushita et al. |
| 4,847,424 A | 7/1989 | Matsushita et al. |
| 4,877,909 A | 10/1989 | Mizusaki et al. |
| 4,879,420 A | 11/1989 | Ernst |
| 4,880,937 A | 11/1989 | Matsushita et al. |
| 4,910,177 A | 3/1990 | Matsushita et al. |
| 5,210,363 A | 5/1993 | Sweeney |
| 5,354,915 A | 10/1994 | Reichle |
| 5,536,854 A | 7/1996 | Weyer et al. |
| 5,576,467 A | 11/1996 | Takahashi et al. |
| 5,840,928 A | 11/1998 | Satoh et al. |
| 5,856,527 A | 1/1999 | Beavers |
| 5,856,531 A | 1/1999 | Beavers |
| 5,912,364 A | 6/1999 | Beavers |
| 5,945,549 A | 8/1999 | Beavers |

FOREIGN PATENT DOCUMENTS

| | | |
|---|---|---|
| EP | 727422 | 8/1996 |
| EP | 747373 | 12/1996 |
| JP | 8-217708 | 8/1996 |
| JP | 8-217770 | 8/1996 |
| JP | 8-217771 | 8/1996 |
| JP | 8-291158 | 11/1996 |
| JP | 39965 | 2/2001 |
| JP | 163866 | 6/2001 |
| JP | 226366 | 8/2001 |

OTHER PUBLICATIONS

Dar'eva et al, J. Gen. Chem. Russ, vol. 29, (1959), pp. 620–625.
Rylander, Catalytic Hydrogenation Over Platinum Metals, Academic Press, Inc., New York, (1967), pp. 229–237.
Fieser & Fieser, Reagents for Organic Synthesis, John Wiley & Sons, Inc., New York (1967), pp. 581–595.
Hino et al, Bull. Chem. Soc. Jpn., vol. 67, No. 5, 1994, pp. 1472–1474.
Santiesteban et al, Journal of Catalysis, vol. 168, 1997, pp. 431–441.
Lopez–Salinas et al, Applied Catalysis A: General 193, 2000, pp. 215–225.
Takahashi et al, Chemistry Letters, 1989, pp. 1141–1144.
Haslam, Tetrahedron, vol. 36, 1980, pp. 2409–2433.
Hurd et al, J. Am. Chem. Soc., 1938, vol. 60, pp. 2419–2425.
Marker et al, J. Am. Chem. Society, 1938, vol. 60, pp. 2440–2442.

*Primary Examiner*—Ba K. Trinh
(74) *Attorney, Agent, or Firm*—Michael J. Blake; Bernard J. Graves, Jr.

(57) ABSTRACT

Disclosed is a process for the preparation of 3-methyltetrahydrofuran (MeTHF) from 3-(hydroxymethyl) tetrahydrofuran (HOMeTHF) by contacting HOMeTHF with hydrogen in the presence of an acidic, supported catalyst comprising a Group VIII metal.

8 Claims, No Drawings

PROCESS FOR THE PREPARATION OF 3-METHYLTETRAHYDROFURAN

FIELD OF THE INVENTION

This invention pertains to a novel process for the preparation of 3-methyltetrahydrofuran (MeTHF) from 3-(hydroxymethyl)tetrahydrofuran (HOMeTHF). More specifically, this invention pertains to a process for the conversion of HOMeTHF to MeTHF by contacting HOMeTHF with hydrogen in the presence of an acidic, supported catalyst comprising a Group VIII metal.

BACKGROUND OF THE INVENTION

MeTHF has been produced in commercial quantities by the high pressure hydrogenation of citraconic anhydride and some of its derivatives according to the procedures disclosed in U.S. Pat. No. 5,536,854 and Published Japanese Patent Application (Kokai) 08-217,771. Since citraconic acid is formed from citric acid or, more economically, as a minor by-product, during maleic anhydride production, these routes to MeTHF are expensive and use a starting material which is not plentiful.

Processes for the production of MeTHF based on less expensive precursors and precursors independent of the production of other materials have been developed. Thus, U.S. Pat. No. 3,932,468, describes a process for isomerizing isoprene monoepoxide into 4-methyl-2,3-dihydrofuran using a nickel and hydrohalic acid catalyst. Although the hydrogenation of 4-methyl-2,3-dihydrofuran into MeTHF is relatively simple, the synthesis of the starting material, isoprene monoepoxide, is not. For example, the preparation of isoprene monoepoxide would require the use of classical (and expensive) epoxide manufacturing techniques such as the use of halohydrins or co-oxidation with aldehydes. Japanese Published Patent Application (Kokai) JP 08-291,158 describes another method for preparing MeTHF in which propylene is converted into 2-methylsuccinate esters by a double oxidative carbonylation in the presence of an alcohol. Although the reductive cyclization of the 2-methylsuccinate esters to MeTHF is facile, the double oxidative carbonylation reaction usually gives limited yields of the dicarbonylated products and requires expensive, reactive solvents to keep the reagents anhydrous.

Another method for the synthesis of MeTHF is disclosed in U.S. Pat. No. 3,859,369 and comprises the hydroformylation and reduction of 2-buten-1,4-diol into 2-methyl-1,4-butanediol which is converted to MeTHF by acid catalysis. U.S. Pat. Nos. 4,590,312 and 4,879,420 describe the conversion of 4-hydroxybutyraldehyde and its immediate precursor, 2-buten-1,4-diol, into MeTHF by reductive alkylation with formaldehyde followed by acid-catalyzed cyclization. In each case, the products were mixtures of MeTHF and tetrahydrofuran, which occurs in the hydroformylation process because isomerization accompanies the hydroformylation, limiting the yield of MeTHF by forming a tetrahydrofuran precursor. In the reductive alkylation processes, the intermediate products as well as the starting materials may form alcohols by hydrogenation. Only those hydrogenations occurring after an initial aldol condensation of the reactants with formaldehyde can form MeTHF. All other hydrogenations gave tetrahydrofuran or other byproducts.

The preparation of MeTHF also is disclosed in Published European Patent Application EP 0 727 422 and involves the hydrocyanation of methacrylate esters. A series of hydrolyses and esterifications form a diester which may be reductively cyclized to MeTHF using an acidic, copper chromite catalyst. In this case, not only were the starting materials expensive (although not as expensive as the citraconic anhydride derivatives), but also the synthesis required four steps. Japanese Published Patent Application (Kokai) JP 08-217,708 describes a process for producing MeTHF by the hydroformylation of methacrylate esters to form mixtures of the α-formylisobutyrate and the β-formylisobutyrate esters using synthesis gas. Japanese Published Patent Application (Kokai) JP 08-217,770 discloses a similar hydroformylation using methyl formate as the C-1 source. In both of these hydroformylation processes, hydrogenation of the resulting β-formylisobutyrate ester over a copper chromite catalyst produced MeTHF. One further hydroformylation route reported in Published European Patent Application Publication EP 747,373 consists of (1) the hydroformylation of isobutenyl alcohol (2-methyl-2-propen-1-ol) to form 4-hydroxy-3-methylbutyraldehyde which (2) was readily hydrogenated with nickel catalysts to 2-methyl-1,4-butanediol and which (3) was cyclized to MeTHF by acid catalysis.

Japanese Published Patent Application (Kokai) JP 2001-226366 (Kuraray Co. Ltd.) discloses dehydrating 3-hydroxy-3-methyltetrahydrofuran in the presence of an acidic substance to produce 3-methyldihydrofuran which may be hydrogenated to 3-methyltetrahydrofuran. Japanese Published Patent Applications (Kokai) JP 2001-039965 and JP 2001-163866 (Kuraray Co. Ltd.) disclose the preparation of 3-hydroxy-3-methyltetrahydrofuran by oxidizing 3-methyl-3-buten-ol with hydrogen peroxide in the presence of a zeolite. This method has limitations for commercial use since it requires relatively expensive and potentially explosive hydrogen peroxide.

U.S. Pat. No. 5,856,527 discloses a process for the preparation of 3-alkyltetrahydrofurans by a two-step process, wherein 2,3-dihydrofuran is reacted with an acetal to form an intermediate compound, which may be converted to a 3-alkyltetrahydrofuran by contacting the intermediate with hydrogen in the presence of a catalytic amount of a Group VIII noble metal or rhenium and a strong acid catalyst. U.S. Pat. No. 5,856,531 discloses a two-step process wherein (1) 2,3-dihydrofuran is reacted with a trialkyl orthoformate in the presence of an acidic catalyst to produce 2-alkoxy-3-dialkoxymethyl)-tetrahydrofuran, and (2) the intermediate is contacted with hydrogen in the presence of a catalyst system comprising a Group VIII noble metal or rhenium and a strong acid to convert the intermediate to a mixture of MeTHF and HOMeTHF.

U.S. Pat. No. 5,912,364 discloses the preparation of MeTHF by contacting 3-formyltetrahydrofuran (3-FTHF) with hydrogen in the presence of a catalyst system comprising a Group VIII noble metal or rhenium and a strong acid under hydrogenolysis conditions of temperature and pressure. The disclosed process typically produces a mixture of MeTHF and HOMeTHF. This patent also discloses processes for the preparation of 3-FTHF by contacting 2,5-dihydrofuran with synthesis gas comprising carbon monoxide and hydrogen in the presence of a rhodium-phosphorus catalyst system according to known hydroformylation procedures. U.S. Pat. No. 5,945,549 discloses a process for the recovery of an aqueous solution of 2- and 3-formyltetrahydrofurans (FTHF's) produced by the rhodium-catalyzed hydroformylation of 2,5-dihydrofuran wherein the FTHF's are recovered as an equilibrium mixture of 2- and 3-FTHF and their hydrates (2- and 3-[di(hydroxy)methyl]tetrahydrofuran) from a hydroformylation product solution comprising a rhodium catalyst, 2- and 3-FTHF and an organic hydroformylation solvent. These known methods for the production of MeTHF starting with 3-FTHF suffer from one or more disadvantages such as low reaction yields, the co-production of other compounds, which have limited utility and/or the use of corrosive acids.

BRIEF SUMMARY OF THE INVENTION

A process has been developed for the conversion of HOMeTHF to MeTHF by contacting HOMeTHF with hydrogen in the presence of certain acidic, supported catalysts. In its broader aspects, the present invention provides a process for the preparation of MeTHF which comprises contacting HOMeTHF with hydrogen in the presence of an acidic, supported catalyst comprising a Group VIII metal such as nickel, cobalt, platinum, palladium, and the like on a catalyst support material under hydrogenation conditions of temperature and pressure.

The MeTHF produced in accordance with the present invention is useful as an industrial solvent and, more importantly, as a monomer in the manufacture of polymers such as elastomers. MeTHF is used extensively as a co-monomer for elastomers giving modified glass transition temperatures and broader elastic ranges.

DETAILED DESCRIPTION OF THE INVENTION

The process of the present invention provides a means for the preparation of MeTHF by contacting HOMeTHF with hydrogen gas in the presence of a catalytically-effective amount of an acidic, supported catalyst comprising (i) a Group VIII metal and (ii) an acidic catalyst support material. The hydrogenation process may be carried out at a total pressure of about 1 to 690 bars gauge (barg; about 15 to 10,012 pounds per square inch—psig), more typically at a pressure of 10 to 68 barg, and preferably at a pressure of 13 to 55 barg. The temperature at which the process is carried out may be in the range of about 200 to 500° C., preferably about 260 to 350° C. The reaction time required to give satisfactory results will vary significantly depending upon a number of process variables such as process temperature and pressure and the particular catalyst employed. The process preferably is operated in a manner that conversion of the HOMeTHF reactant is maintained below 85 mole percent to maximize conversion to MeTHF product and minimize conversion to by-products.

The process of the present invention normally is carried out in the liquid phase in the presence of an extraneous solvent, typically an inert solvent, i.e., a solvent, which is non-reactive under the process conditions. Water is a convenient solvent when 3-formyl THF (3-FTHF), from which the HOMeTHF starting material may be derived, is recovered from a hydroformylation process according to the process described in U.S. Pat. No. 5,945,549. However, polar solvents compatible with water and the high reaction temperatures may be used. Examples of such polar solvents include tetrahydrofuran, tetrahydropyran, alkanols such as isopropanol, ethanol, methanol, and butanol, and the ethylene glycol ethers such as 1,2-dimethoxyethane, bis(2-methoxyethyl) ether, and 2,5,8,11-tetraoxadodecane. The amount of solvent used may vary from about 1 to 99 parts by weight per part by weight of the HOMeTHF reactant. More common amounts of solvent although not necessarily preferred are 10 to 90 parts by weight solvent per part by weight of the HOMeTHF reactant with 20 to 80 parts solvent (same basis) being most common.

The catalysts useful in the process of the present invention are acidic, supported catalysts comprising a Group VIII metal, e.g., nickel, cobalt, platinum, palladium, and the like, on an acidic catalyst support material. Examples of the support material include alumina, zirconia, silica, titania, vanadium oxide, molybdenum oxide, and mixed metal oxides comprising any combination of zirconium, aluminum, titanium, cerium, calcium, silicon, magnesium, copper, barium, chromium, manganese, vanadium, iron, and strontium such as zirconium-titanium and molybdenum-zirconium mixed oxides. The support material also may be selected from salts having low solubility in water and organic solvents such as, for example, the phosphate, monohydrogen phosphate, dihydrogen phosphate, sulfate, monohydrogen sulfate titanate, zirconate, chromate, vanadate, aluminate, and silicate salts of aluminum, zirconium, titanium, neodymium, niobium, molybdenum, cerium, and other rare earth metals. The preferred support materials are zirconium oxide, aluminum oxide, and zirconium phosphate. The amount of Group VIII metal which may be present on the support material may vary from about 0.001 to 50 weight percent, more typically about 1 to 20 weight percent, based on the total weight of the catalyst. The amount of Group VIII depends, in part, upon the particular metal used. For example, a supported nickel catalyst may contain up to about 60 weight percent nickel, e.g., from about 1 to 60 weight percent nickel, whereas a supported palladium catalyst typically contains less metal, e.g., up to about 0.1 to 5 weight percent palladium. The preferred acidic, supported catalysts comprise about 1 to 15 weight percent nickel on a catalyst support material selected from aluminum oxide, zirconium oxide, molybdenum oxide, and zirconium phosphate.

The supported catalysts useful in the present invention comprise acidic catalysts. The acidity of the solid acidic catalysts can be measured and characterized according to known techniques and procedures, for example, Temperature-Programmed Desorption (TPD) using ammonia, monomethylamine or pyridine. See, for example, Tanabe, et al., New Solid Acids and Bases and their Catalytic Properties, Vol. 51, Elsevier Science Publishing Company, Inc., New York (1989). By "acidic catalysts" we mean catalysts which have acid site densities of greater than about $6 \times 10^5$, preferably greater than about $1 \times 10^6$, acid sites per square meter as measured by TPD using monomethylamine. The catalyst support material may be alumina, titania, zirconia, molybdenum oxide, vanadium oxide or a mixed oxide which can be rendered more acidic by the addition of a Brønsted acid to the unmodified catalyst support material. Examples of Brønsted acids which may be used include inorganic acids such as sulfuric, phosphoric and hydrohalic acids, e.g., hydrogen chloride, hydrogen bromide and hydrogen iodide. The Brønsted acid also may be an organic acid such as carboxylic acids, e.g., acetic acid, or a sulfonic acid, e.g., an alkyl- or aryl-sulfonic acid. Acidification of the catalyst may occur prior to and/or after the deposition of the Group VIII metal. Alternatively, the acidic catalysts employed in the present invention may comprise a support material containing an inherently acidic oxide such as the oxides of niobium, neodymium, molybdenum, tungsten, silicon and boron. The presence of one or more oxides of Group VB–VIIB is known to increase the acidity of Group III and Group IV metal oxides such as alumina, zirconia, ceria, and the like. See, for example, Makoto Hino and Kazushi Arata, *Bull. Chem. Soc. Jpn.*, 67, 1472–1474, (1994); J. G. Santiesteban, J. C. Vartuli, S. Han, R. D. Bastian, and C. D. Chang, *Journal of Catalysis*, 168, 431–441 (1997); and E. Lopez-Salinas, J. G. Hernandez-Cortez, I. Schifter, E. Torres-Garcis, J. Navarrete, A. Gutierrez-Carrillo, T. Lopez, P. P. Lottici, D. Bersani, *Applied Catalysis A: General* 193, 215–225, (2000). The catalyst support material also may comprise a hetero-poly-acid having Keggin type structure and based on silica, tungsten, molybdenum and/or phosphorus. Specific examples of such acidic oxides and hetero-poly-acids include zirconia with molybdenum oxide, zirconia with tungsten oxide, silicotungstic acid $H_4O_{40}SiW_{12}$, phosphotungstic acid hydrate $H_3O_{40}PW_{12}$, 12-molybdophosphoric acid $H_3MoO_7P$, 12-tungstophosphate $H_3O_7PW$, and the like.

The acidic catalysts, which may be employed advantageously in the hydrogenation process of the present invention include certain catalysts which are commercially available such as Criterion Catalyst 424 (C-424) comprising 3.0–4.5 weight percent nickel on alumina modified with phosphorus (6.0–9.0%) and molybdenum (16.5–22.5%) oxides. Alternatively, useful acidic catalysts may be prepared using procedures known to those skilled in the art.

The catalytic hydrogenation process of the present invention is carried out without co-feeding a strong acid, iodine or iodine compound according to the process described in U.S. Pat. No. 5,912,364.

Prior to their use, the catalysts comprising one or more catalytically-active Group VIII metals deposited on a catalyst support material are reduced with hydrogen to convert the metal salts into zero valent active metal catalyst. This pre-reduction generally takes place at temperatures between 200° C. and the calcining temperature with 250 to 500° C. being more preferred and 300 to 400° C. most preferred.

The process provided by the present invention provides a means for the production of MeTHF from HOMeTHF. The HOMeTHF may be obtained by contacting FTHF with hydrogen gas in the presence of a catalytically-effective amount of a hydrogenation catalyst comprising a Group VIII metal and under hydrogenation conditions of pressure and temperature which converts the FTHF to HOMeTHF. Thus, a second embodiment of our invention concerns a process for the preparation 3-methyltetrahydofuran (MeTHF) by the steps comprising:

(1) contacting 3-formyltetrahydrofuran (FTHF) with hydrogen in the presence of a hydrogenation catalyst comprising a Group VIII metal under hydrogenation conditions of pressure and temperature to convert the FTHF to 3-(hydroxymethyl)tetrahydrofuran (HOMeTHF); and (2) contacting the HOMeTHF produced in step (1) with hydrogen in the presence of an acidic, supported catalyst comprising (i) a Group VIII metal and (ii) an acidic catalyst support material under hydrogenation conditions of temperature and pressure to convert HOMeTHF to MeTHF.

The catalyst utilized in step (1) preferably is a supported nickel catalyst containing up to about 60 weight percent nickel, e.g., from about 1 to 60 weight percent nickel, based on the total weight of the catalyst. The preferred step (1) supported catalysts comprise about 1 to 15 weight percent nickel on a catalyst support material. Steps (1) and (2) of the second embodiment of the present invention may utilize the same catalyst, i.e., an acidic, supported catalyst comprising (i) a Group VIII metal and (ii) an acidic catalyst support material, wherein milder conditions of temperature and/or pressure are employed in step (1) to produce HOMeTHF, or primarily HOMeTHF. Step (1) of the second embodiment, like the second step, normally is carried out in the liquid phase in the presence of an extraneous solvent, typically an inert solvent, i.e., a solvent, which is non-reactive under the process conditions. Water is a convenient solvent when 3-FTHF is recovered from a hydroformylation process. However, polar solvents, such as those described above, which are compatible with water and the high reaction temperatures also may be used in the first step.

EXAMPLES

The synthesis of catalysts useful in the hydrogenation process provided by the present invention and the operation of the hydrogenation process are further illustrated by the following examples. All percentages given in the examples are by weight unless specified otherwise. As used herein, the percent conversion of HOMeTHF (or 3-FTHF) is:

$$\frac{\text{Moles HOMeTHF (or 3-FTHF) Converted to All Products}}{\text{Moles HOMeTHF (or 3-FTHF) Fed}} \times 100$$

and percent selectivity to a compound is:

$$\frac{\text{Moles HOMeTHF (or 3-FTHF) Converted to a Compound}}{\text{Moles HOMeTHF (or 3-FTHF) Converted to All Products}} \times 100$$

Products were analyzed by gas chromatography (GC) using a Hewlett Packard Series 6890 Gas Chromatograph equipped with a thermal conductivity detector (helium flow of 1 cc/minute and a split of 100:1). The column was a 30 meter, DB-1 capillary column with a 0.04 mm film thickness.

Catalyst Example A

Zirconium nitrate (115.5 g, 0.5 mol) was dissolved in 2000 ml of water. A 28% aqueous ammonia solution was added dropwise with occasional stirring with a glass rod until a pH of 10–11 was achieved. The resulting precipitate was washed with deionized water. A solution of nickel nitrate (58.0 g, 0.2 mol) and molybdic acid (3.39 g, 0.01 mol) in 50 ml of water was added to the precipitate followed by addition of 21.8 ml (0.4 mol) of 28% aqueous ammonia. The resulting suspension was dried at room temperature for 5 hours and at 110° C. for 5 hours. It was then calcined at 400° C. for 10 hours. The resulting catalyst comprising nickel, molybdenum, and hydrous zirconia was reduced under hydrogen for 3 hours at 300° C. The Zr:Mo:Ni atomic ratio of the catalyst (Catalyst A) thus prepared was 50:1:20.

Catalyst Example B

Zirconium hydroxide was precipitated by adding aqueous ammonia (28%, 45 ml, 0.36 mol) to a solution of zirconyl sulfate (31.95 g, 0.09 mol) in 1000 ml of water. The precipitate was washed with de-ionized water. In a separate flask potassium hydroxide (3.36 g, 0.06 mol) solution in water (20 ml) was added to a solution of nickel nitrate (8.70 g, 0.03 mol) in 100 ml of water. Nickel hydroxide precipitate was washed with de-ionized water and combined with zirconium hydroxide. To the resulting mixture was added a solution of molybdic acid (1.02 g, 0.003 mol) in water (5 ml). The mixture was well stirred with a glass rod, dried in air for 5 hours at room temperature, and for 5 hours at 110° C., then calcined at 400° C. for 10 hours. The catalyst was reduced under hydrogen for 3 hours at 300° C. The Zr:Mo:Ni atomic ratio of the catalyst (Catalyst B) thus prepared was 30:1:10.

Catalyst Example C

Silica gel (20.9 g, 0.28 mol) was dissolved in aqueous KOH (23.52 g, 0.42 mol) in 50 ml water. The resulting solution was added dropwise to a solution of zirconyl sulfate (35.5 g, 0.1 mol) and nickel nitrate (2.90 g, 0.01 mol) in water with constant stirring at 60–80° C. After two hours, the precipitate was washed with water, dried at room temperature for 5 hours and at 110° C. for 5 hours. It was then calcined at 400° C. for 10 hours. The resulting catalyst, nickel on mixed silica-zirconia support, was reduced under hydrogen for 2 hours at 300° C. The Zr:Si:Ni atomic ratio of the catalyst (Catalyst C) thus obtained was 10:28:1.

Catalyst Example D

Silica gel (1.85 g, 0.025 mol) was dissolved in aqueous KOH (12.32 g, 0.22 mol) in 50 ml water. The resulting solution was added dropwise to a solution of zirconyl sulfate (17.75 g, 0.05 mol) and nickel nitrate (2.91 g, 0.01 mol) in water under constant stirring at 60–80° C. After two hours, the precipitate was washed with water, dried at room temperature for 5 hours and at 110° C. for 5 hours. It was then calcined at 400° C. for 10 hours. The resulting nickel on the mixed silica-zirconia support catalyst was reduced under hydrogen for 2 hours at 300° C. The Zr:Si:Ni atomic ratio of the catalyst (Catalyst D) thus obtained was 10:5:2.

Catalyst Example E

Silica gel (3.70 g, 0.05 mol) was added to a solution of KOH (19.60 g, 0.35 mol) in 50 ml water. The solution was stirred until all of the silica had dissolved. The resulting solution of sodium silicate and KOH was added dropwise to a solution of zirconyl sulfate (17.75 g, 0.05 mol) and nickel nitrate (14.54 g, 0.05 mol) in 1000 ml of water under constant stirring at 60–80° C. After two hours, the precipitate was washed with water, dried at room temperature for 5 hours and at 110° C. for 5 hours. It was then calcined at 400° C. for 10 hours. The resulting nickel on mixed silica-zirconia catalyst was reduced under hydrogen for 2 hours at 300° C. The Zr:Si:Ni atomic ratio of the catalyst (Catalyst E) was 1:1:1.

Catalyst Example F

A solution of sodium hydroxide (20.0 g, 0.5 mol) in water (100 ml) was added to a solution of zirconyl sulfate (35.5 g, 0.1 mol) and nickel nitrate (14.5 g, 0.05 mol) in water (1000 ml) under constant stirring at 60–80° C. After 24 hours, the precipitate was washed with water, and combined with solution of $NbCl_5$ (1.35 g, 0.005 mol) in isopropanol (10 ml), dried at room temperature for 5 hours and at 110° C. for 5 hours. It was then calcined at 400° C. for 10 hours. The resulting nickel and niobium-containing zirconia catalyst was reduced under hydrogen for 2 hours at 300° C. The Zr:Nb:Ni atomic ratio of the catalyst (Catalyst F) was 20:1:10.

Catalyst Example G

Silica gel (3.70 g, 0.05 mol) was dissolved in a solution of KOH (16.8 g, 0.30 mol) in 50 ml water. The resulting solution was added drop wise to a solution of aluminum nitrate nonahydrate (18.75 g, 0.05 mol) and nickel nitrate (14.54 g, 0.05 mol) in 1000 ml of water under constant stirring at 60–80° C. After two hours, the precipitate was washed with water, dried at room temperature for 5 hours and at 110° C. for five hours. It was then calcined at 400° C. for 10 hrs. The resulting nickel on mixed silica-alumina catalyst was reduced under hydrogen for 2 hours at 300° C. The Al:Si:Ni atomic ratio of the catalyst (Catalyst G) was 1:1:1.

Catalyst Example H

A commercial nickel molybdate powder was reduced under hydrogen for 2 hours at 300° C. The Mo:Ni atomic ratio of the resulting catalyst (Catalyst H) was 1:1.

Catalyst Example J

A commercial nickel molybdate in the form of a powder was mixed with water and then dried at 110° C. for 5 hours. It was then calcined at 400° C. for 10 hours. The resulting nickel-molybdenum catalyst in a granular form was reduced under hydrogen for 2 hours at 300° C. The Mo:Ni atomic ratio of the catalyst (Catalyst J) was 1:1.

Hydrogenation Examples 1–13

A 300 ml autoclave was charged with 3-FTHF (10.0 g, 0.1 mol), water (10.0 g, 0.55 mol), and a catalyst (5.0 g) selected from C-424 or one of the catalysts prepared according to the preceding examples. The autoclave was flushed with hydrogen three times at 3.45 barg (50 psig) pressure. The initial hydrogen pressure was set at 13.78 barg (200 psig) pressure. The autoclave was stirred and heated for 1–2 hours at 150° C. During that time, the reaction progress was monitored by GC analysis of samples obtained from the autoclave through a sampling tube. When the conversion of 3-FTHF to HOMeTHF was essentially complete, the autoclave temperature was raised and stirring continued for an additional one hour at 250–300° C. The crude mixture was analyzed by GC. The conversion of HOMeTHF and the selectivities to MeTHF and to other products achieved during that last one hour hydrogenation period at 250–300° C. are shown in Table I wherein "Temp" is the temperature (°C.) at which that last one hour of each hydrogenation was carried out, "THF" is tetrahydrofuran, "BuOH" is 1-butanol, "MeBuOH" is 2-methyl-1-butanol, "MeGBL" is 3-methyl-gamma-butyrolactone, "Other" refers to selectivities to one or more of 2-propanol, 3-methylfuran and/or 3-methyldihydrofuran, and "Conv" is the mole percentage of HOMeTHF that was converted to products.

TABLE I

| Example No. | Catalyst | Temp | Selectivity | | | | | | Conv |
|---|---|---|---|---|---|---|---|---|---|
| | | | MeTHF | MeGBL | MeBuOH | THF | BuOH | Other | |
| 1 | C | 280 | 60.95 | 23.98 | 1.32 | 2.13 | 2.65 | 0 | 75.44 |
| 2 | D | 280 | 70.51 | 13.47 | 4.43 | 2.98 | 3.83 | 0 | 90.25 |
| 3 | E | 300 | 72.40 | 10.35 | 7.83 | 3.67 | 4.90 | 0 | 97.88 |
| 4 | G | 280 | 64.61 | 23.20 | 0 | 2.09 | 4.40 | 0.90 | 85.02 |

TABLE I-continued

| Example No. | Catalyst | Temp | Selectivity | | | | | | Conv |
|---|---|---|---|---|---|---|---|---|---|
| | | | MeTHF | MeGBL | MeBuOH | THF | BuOH | Other | |
| 5 | A | 280 | 87.59 | 2.23 | 4.21 | 2.37 | 1.29 | 0.80 | 98.56 |
| 6 | B | 300 | 81.00 | 5.13 | 4.05 | 2.57 | 1.57 | 1.74 | 95.40 |
| 7 | B | 280 | 82.83 | 5.34 | 3.18 | 3.32 | 1.29 | 0.93 | 99.09 |
| 8 | H | 300 | 66.31 | 11.21 | 5.65 | 3.12 | 3.16 | 2.32 | 93.32 |
| 9 | H | 280 | 72.52 | 10.49 | 4.77 | 2.79 | 3.17 | 1.92 | 93.70 |
| 10 | F | 250 | 82.88 | 6.10 | 3.07 | 3.03 | 0 | 0 | 48.82 |
| 11 | F | 280 | 77.21 | 2.98 | 1.46 | 3.35 | 0.91 | 0.87 | 100.0 |
| 12 | J | 280 | 55.11 | 11.95 | 5.88 | 12.9 | 3.80 | 3.81 | 99.15 |
| 13 | C-424 | 280 | 79.18 | 5.89 | 1.12 | 3.06 | 0 | 1.41 | 97.94 |

Examples 14–24

These examples describe the continuous production of MeTHF starting with 3-FTHF and using two hydrogenation reactors. The first reactor comprised a 43.2 cm (17 inches) section of stainless steel tubing having an inside diameter of 12.5 mm (0.5 inch). The first reactor was loaded with 40 ml of a commercially-available, supported, nickel catalyst comprising 50 weight percent nickel on silica-alumina (Engelhard 3276). The second reactor comprised an 88.9 cm (35 inches) section of stainless steel tubing also having an inside diameter of 12.5 mm (0.5 inch). The second reactor was filled with 250 ml of another commercially-available catalyst, Criterion 424 catalyst (C-424, described previously). The temperatures in each reactor were controlled separately with thermocouples located at the middle of each catalyst bed. Heating was provided via electrical furnaces (Applied Test Systems, Inc.) enclosing each reactor. The product exiting the second reactor was cooled by a glycol chilled condenser and fed to a product tank consisting of a 1.22 m (4 feet) long cylinder having a diameter of 5.08 cm (2 inches) which also served as a vapor/liquid separator. The capacity of the product tank was 2 liters.

A 40% aqueous solution of 3-FTHF was pumped into the top of the first reactor through a Mini-pump from the Thermol Separator Products Corp at a rate of 37–55 ml/hour along with varying amounts of hydrogen. Concurrently, a stream of hydrogen gas was fed with the pressure maintained by means of a pressure transducer/control valve feedback loop and a constant flow of gas ensured through a metering valve attached to the vapor/liquid separator located at the exit of the second reactor and through which a flow of 50 cc/minute was maintained. The two reactors were connected by a 3.2 mm (⅛ inch) stainless steel tube connected from the bottom of the first reactor into the top of the second. This arrangement allowed both reactors to maintain a trickle-bed mode of operation with the product from the first reactor leading directly into the second.

The product exiting each reactor was sampled through a sampling valve connected to the bottom of each reactor and analyzed by GC. The final product was recovered from the product tank by separating the aqueous and organic layers. The aqueous layer was partially steam distilled to recover the volatile components boiling below 100° C. consisting mostly of MeTHF and several by-products. The overhead distillate from this column was returned to the aqueous/organic separator. The base overflow from this column eventually containing all water in the system fed into a second fractional distillation column operating at 100 mm pressure in which the water was removed overhead and a concentrated solution of unconverted HOMeTHF was recovered. The organic product recovered from the aqueous/organic separator was fractionally distilled to recover crude MeTHF and MeTHF/alcohol azeotropes with the base material containing the residual water, which was returned to the aqueous/organic separator. The combined MeTHF and MeTHF/alcohol azeotrope distillate from this column was fed to another fractional distillation column operating at approximately 1 barg. In this column, the materials were combined with an equal volume of toluene and distilled. The distillate from this column consisted of toluene/alcohol low boilers. The alcohols could be separated from the toluene by washing with water. The base material from this column consisting of toluene and MeTHF was fed to another fractional distillation column where pure MeTHF distilled overhead (b.p. 87° C.) and the toluene in the base overflow was returned to the first organic distillation column.

The process conditions and feed rates and the results obtained in each of Example 15–25 are shown in Table II wherein "Feed Rate" is the ml of 40% aqueous 3-FTHF fed to the first reactor per hour, "$H_2$ Flow" is the volume (liters) of hydrogen fed to the first reactor per hour, "Feed Ratio" is the moles hydrogen per mole 3-FTHF fed to the first reactor, "Temp" is the temperature (°C.) measured in the middle of the second reactor, "Press" is the total pressure (barg) within the two reactors, "MeTHF Yield" (%) is based on the amount of 3-FTHF consumed, "MeTHF Select" (%) is the selectivity of the conversion of 3-FTHF to MeTHF, "Time" (hours) is the period of time during which product samples were collected, "Conv" (%) refers to the second reactor conversion, i.e., the conversion of HOMeTHF to other products assuming 100% conversion and selectivity to HOMeTHF in the first reactor, and "Prod Rate" is the amount (g) of MeTHF produced per hour per liter of catalyst in the second reactor.

TABLE II

| Example No. | Feed Rate | $H_2$ Flow | Feed Ratio | Temp | Press | MeTHF Yield | MeTHF Select | Conv | Time | Prod Rate |
|---|---|---|---|---|---|---|---|---|---|---|
| 14 | 37.1 | 42.5 | 13.09 | 295 | 37.9 | 40.9 | 41.9 | 97.57 | 21 | 20.4 |
| 15 | 37.5 | 84.9 | 25.93 | 295 | 37.9 | 21.1 | 22.0 | 95.78 | 24 | 10.6 |

TABLE II-continued

| Example No. | Feed Rate | H₂ Flow | Feed Ratio | Temp | Press | MeTHF Yield | MeTHF Select | Conv | Time | Prod Rate |
|---|---|---|---|---|---|---|---|---|---|---|
| 16 | 55.0 | 84.9 | 17.68 | 290 | 37.9 | 12.2 | 28.3 | 43.12 | 24 | 9.0 |
| 17 | 53.5 | 42.5 | 9.09 | 295 | 55.1 | 26.5 | 62.8 | 42.22 | 24 | 19.1 |
| 18 | 37.8 | 28.3 | 8.59 | 295 | 55.1 | 66.4 | 69.9 | 95.04 | 24 | 33.7 |
| 19 | 38.5 | 14.2 | 4.21 | 275 | 55.1 | 33.4 | 78.5 | 42.50 | 17 | 17.2 |
| 20 | 35.5 | 28.3 | 9.13 | 290 | 55.1 | 53.7 | 78.8 | 68.14 | 24 | 25.6 |
| 21 | 37.0 | 28.3 | 8.75 | 295 | 55.1 | 62.5 | 65.4 | 95.51 | 23 | 31.1 |
| 22 | 50.9 | 28.3 | 6.37 | 300 | 55.1 | 44.9 | 90.6 | 49.56 | 25 | 30.7 |
| 23 | 38.0 | 19.0 | 5.71 | 300 | 55.1 | 79.8 | 83.9 | 95.14 | 25 | 40.7 |
| 24 | 37.4 | 19.0 | 5.81 | 300 | 55.1 | 79.8 | 79.8 | 100.0 | 23 | 40.1 |

Examples 25–29

The general procedure described above for Examples 14–24 was used in Examples 25–29 except that 50% aqueous HOMeTHF and hydrogen were fed directly to the second reactor. The results achieved are reported in Table III wherein "Feed Rate", "H₂ Flow", "Feed Ratio", "Press", "MeTHF Yield", "MeTHF Select", "Prod Rate" and "Time" have the meanings given above, "Temp" is the inside reactor temperature (°C.) measured at the middle section of the reactor, and "Conv" (%) refers to the conversion of the HOMeTHF feed.

TABLE III

| Example No. | Feed Rate | H₂ Flow | Feed Ratio | Temp | Press | MeTHF Yield | MeTHF Select | Conv | Prod Rate | Time |
|---|---|---|---|---|---|---|---|---|---|---|
| 25 | 52.5 | 14.2 | 2.38 | 300 | 55.1 | 44.8 | 60.3 | 74.19 | 40.9 | 8 |
| 26 | 38.8 | 7.1 | 1.61 | 308 | 55.1 | 76.2 | 84.1 | 90.59 | 51.5 | 16 |
| 27 | 36.4 | 14.2 | 3.43 | 300 | 55.1 | 66.8 | 67.3 | 99.36 | 42.3 | 8 |
| 28 | 54.4 | 7.1 | 1.15 | 300 | 55.1 | 49.3 | 70.1 | 70.30 | 46.7 | 16 |
| 29 | 36.9 | 7.1 | 1.69 | 300 | 55.1 | 76.4 | 93.7 | 81.48 | 49.0 | 7 |

The acidity and surface area of (1) a commercial supported nickel catalyst, Engelhard 3276 catalyst, comprising 50 weight percent nickel on silica-alumina, (2) Catalyst B and (3) commercial C-424 catalyst was determined according to the following procedures:

Temperature-Programmed Desorption of Monomethylamine

The temperature-programmed desorption (TPD) of monomethylamine (MMA) was carried out in a plug flow reactor (6.35 mm outside diameter) system equipped with an on-line quadrapole mass spectrometer (UTI Model 100). Typically, 0.1 g of catalyst was used. Firstly, a catalyst was treated in flowing hydrogen (Air Products, 99.99% purity) with a flow rate of 100 standard cubic centimeter per minute (sccm) at 300° C. for 3 hours. Then the sample was cooled down to 50° C. in flowing hydrogen. After the temperature stabilized at 50° C., the hydrogen flow was stopped and simultaneously MMA (Matheson, 2000 ppm balanced with nitrogen) was flowed through the reactor at a rate of 100 sccm. Thirty minutes later, the MMA flow was stopped and helium (Air Products, 99.99% purity) was purged through the reactor at a rate of 100 sccm at 50° C. for 30 minutes. Finally, the MMA TPD was started by heating the sample at a rate of 10° C. per minute to 500° C. in 100 sccm He. The desorbed MMA was monitored by the on-line mass spectrometer and mass fragments such as 31, 30, and 29 were used to determine the amount of MMA desorbed from the catalyst. The molar ratio of MMA to acid site was assumed to be one when the amount of MMA was converted to the number of surface acidic sites.

Surface Area Measurement

Nitrogen (Air Product, 99.999%) adsorption at 77 K on the catalysts was performed in a Micromeritics adsorption unit (Model ASAP2000). Typically, 0.3 g of sample was used. Prior to the adsorption, the sample was heated in situ at 300° C. under evacuation (about 1 torr) for 3 hours. The BET method was used to determine the surface area.

The Engelhard 3276 catalyst (5.0 g) was evaluated in the hydrogenation procedure of Examples 1–14 using a temperature of 150–280° C., a pressure of 13.78 barg and a time of 1–2 hours. The acidity of the catalysts and the performance of the Engelhard 3276 (E-3276) catalyst as compared to the results of Catalyst B and commercial CRI 424 catalyst reported in Table I are set forth in Table IV wherein "Surface Area" is square meters per gram, "Nickel Content" is weight percent, "Acid Site Density" is sites per square meter and "Selectivity" for THF and MeTHF and "Conv" have the meanings given for Examples 1–14 and Table I.

TABLE IV

| Catalyst | Surface Area | Nickel Content | Acid Site Density | Selectivity | | Conv |
|---|---|---|---|---|---|---|
| | | | | THF | MeTHF | |
| E-3276 | 159 | 50.0 | $<6 \times 10^5$ | 96.4 | 3.4 | 98.4 |
| B | 118 | 13.3 | $4.70 \times 10^{18}$ | 2.6 | 81.0 | 95.4 |
| C-424 | 158 | 3.0 | $2.82 \times 10^{18}$ | 3.1 | 79.2 | 97.9 |

The Engelhard 3276 (E-3276) catalyst contains calcium which renders the catalyst relatively non-acidic.

The invention has been described in detail with particular reference to preferred embodiments thereof, but it will be understood that variations and modifications can be effected within the spirit and scope of the invention.

We claim:

1. Process for the preparation of 3-methyltetrahydofuran (MeTHF) which comprises contacting 3-(hydroxymethyl) tetrahydrofuran (HOMeTHF) with hydrogen in the presence of an acidic, supported catalyst comprising a Group VIII metal under hydrogenation conditions of temperature and pressure.

2. Process according to claim 1 wherein HOMeTHF is contacted with hydrogen at a pressure of about 10 to 68 bars gauge (barg) and a temperature of about 200 to 500° C. in the presence of an acidic, supported catalyst comprising nickel.

3. Process according to claim 1 wherein HOMeTHF is contacted with hydrogen at a pressure of about 13 to 55 bars gauge (barg) and a temperature of about 260 to 350° C. in the presence of an acidic, supported catalyst comprising about 1 to about 60 weight percent nickel on a catalyst support material selected from aluminum oxide, zirconium oxide, molybdenum oxide, and zirconium phosphate, wherein the acidic catalyst has an acid site density of greater than about $6 \times 10^5$ acid sites per square meter as measured by Temperature-Programmed Desorption using monomethylamine.

4. Process according to claim 2 carried out in the liquid phase in the presence of an inert solvent.

5. Process according to claim 1 wherein an aqueous solution of HOMeTHF is contacted with hydrogen at a pressure of about 13 to 55 bars gauge (barg) and a temperature of about 260 to 350° C. in the presence of an acidic, supported catalyst comprising about 1 to 15 weight percent nickel on a catalyst support material selected from aluminum oxide, zirconium oxide, molybdenum oxide, and zirconium phosphate, wherein the acidic catalyst has an acid site density of greater than about $1 \times 10^6$ acid sites per square meter as measured by Temperature-Programmed Desorption using monomethylamine.

6. Process for the preparation 3-methyltetrahydofuran (MeTHF) by the steps comprising:

(1) contacting 3-formyltetrahydrofuran (FTHF) with hydrogen in the presence of a hydrogenation catalyst comprising a Group VIII metal under hydrogenation conditions of pressure and temperature to convert the FTHF to 3-(hydroxymethyl)tetrahydrofuran (HOMeTHF); and (2) contacting the HOMeTHF produced in step (1) with hydrogen in the presence of an acidic, supported catalyst comprising (i) a Group VIII metal and (ii) an acidic catalyst support material under hydrogenation conditions of temperature and pressure.

7. Process according to claim 6 wherein the catalyst of step (1) comprises nickel deposited on a catalyst support material; and step (2) comprises contacting HOMeTHF with hydrogen at a pressure of about 13 to 55 bars gauge (barg) and a temperature of about 260 to 350° C. in the presence of an acidic, supported catalyst comprising about 1 to about 60 weight percent nickel on a catalyst support material selected from aluminum oxide, zirconium oxide, molybdenum oxide, and zirconium phosphate, wherein the acidic catalyst has an acid site density of greater than about $6 \times 10^5$ acid sites per square meter as measured by Temperature-Programmed Desorption using monomethylamine.

8. Process according to claim 6 wherein step (1) comprises contacting an aqueous solution of FTHF with hydrogen in the presence of a catalyst comprising about 1 to 15 weight percent nickel deposited on a catalyst support material; and step (2) comprises contacting an aqueous solution of HOMeTHF with hydrogen at a pressure of about 13 to 55 bars gauge (barg) and a temperature of about 260 to 350° C. in the presence of an acidic, supported catalyst comprising about 1 to 15 weight percent nickel on a catalyst support material selected from aluminum oxide, zirconium oxide, molybdenum oxide, and zirconium phosphate, wherein the acidic catalyst has an acid site density of greater than about $1 \times 10^6$ acid sites per square meter as measured by Temperature-Programmed Desorption using monomethylamine.

* * * * *